US005487885A

United States Patent [19]

Sovak et al.

[11] Patent Number: 5,487,885
[45] Date of Patent: Jan. 30, 1996

[54] SUNBLOCKING POLYMERS AND THEIR FORMULATION

[75] Inventors: Milos Sovak, La Jolla; Ronald C. Terry; James G. Douglass, III, both of San Diego; Farid Bakir, Del Mar, all of Calif.

[73] Assignee: Biophysica, Inc., La Jolla, Calif.

[21] Appl. No.: 164,881

[22] Filed: Dec. 9, 1993

Related U.S. Application Data

[63] Continuation-in-part of Ser. No. 994,426, Dec. 21, 1992, abandoned.

[51] Int. Cl.$^6$ .............................. A61K 31/78; A61K 7/42
[52] U.S. Cl. .................. 424/59; 526/328; 526/328.5; 526/329.5; 526/329.2; 526/304; 526/307; 526/307.7
[58] Field of Search .............................. 424/59; 526/328, 526/328.5, 329.5, 329.2, 304, 307, 307.7

[56] References Cited

U.S. PATENT DOCUMENTS

| | | | |
|---|---|---|---|
| 3,880,875 | 4/1975 | Strobel et al. | 260/308 A |
| 4,003,990 | 1/1977 | Jacquet | 424/78.32 |
| 4,233,430 | 11/1980 | Jacquet et al. | 526/259 |
| 4,508,882 | 4/1985 | Yoshida et al. | 526/259 |
| 4,524,061 | 6/1985 | Cho | 424/60 |
| 5,041,282 | 8/1991 | Sabatelli | 424/59 |
| 5,063,048 | 11/1991 | Saitoh | 424/59 |
| 5,099,027 | 3/1992 | Vogl et al. | 548/259 |
| 5,134,223 | 7/1992 | Langer | 528/272 |
| 5,204,090 | 4/1993 | Han | 424/59 |
| 5,243,021 | 9/1993 | Langer | 528/272 |
| 5,250,652 | 10/1993 | Langer | 528/125 |
| 5,302,376 | 4/1994 | Forestier et al. | 424/59 |

FOREIGN PATENT DOCUMENTS

WO93/22413  1/1993  WIPO.

OTHER PUBLICATIONS

Dromgoole, et al. (1990) Sunscreening agent intolerance, contact and photocontact sensitization and contact urticaria. J. Amer. Derm. 22:1068–1078.

Lowe (1990) Photoprotection. Sem Derm. 9:78–83.

*Primary Examiner*—Peter F. Kulkosky
*Attorney, Agent, or Firm*—Bertram I. Rowland

[57] ABSTRACT

Novel polymeric compositions and their intermediates are provided, providing for broad range protection from ultraviolet radiation. Acryl polymers comprising at least two different ultraviolet absorbing moieties having different light absorbing ranges are employed in conjunction with another hydrophilic monomer to provide sunscreen formulations for invisibility, and enhanced protection, without deleterious effects in the dermis.

5 Claims, No Drawings

SUNBLOCKING POLYMERS AND THEIR FORMULATION

CROSS-REFERENCE TO RELATED APPLICATIONS

This application is a continuation-in-part of application Ser. No. 07/994,426, filed Dec. 21, 1992, now abandoned.

INTRODUCTION

1. Technical Field

The field of this invention is sunblock compositions for use in dermatological and ophthalmological applications.

2. Background

The role of ultraviolet radiation and skin aging in development of skin cancer, as well as eye cataracts, is being increasingly recognized. For the protection of the skin, the state of art utilizes various UV-absorbing compounds, primarily singular (monomeric) aromatic compounds, formulated into creams and lotions. Intraocular and contact soft lenses are described with such compounds added into the hydrogel, or coating the lens surfaces with UV-absorbing preparations. Ophthalmologic solutions are described which claim protection against UV radiation using various compounds added to standard eyedrop formulations.

There are many disadvantages to the known UV blockers. One is their lack of biological tolerance. Due to their toxicity and allergenicity, as well as other side-effects, the amounts of the various UV-absorbing additives are strictly limited and regulated. The protection which they afford is limited by their toxicity potential. Also, as these UV-blocking compounds penetrate into the skin, they convert the absorbed UV radiation into heat, which in turn dilates the vessels which is perceived as unpleasant.

For ophthalmic use, the protection afforded by the ophthalmic solutions containing the toxic monomers is inefficient. The concentration limitation imposed by the toxicity of the compounds prevents formulations providing adequate protection. In hydrogel lenses, the monomers leak out. Coating such lenses in a permanent way is, on the other hand, difficult and costly.

An ideal sun radiation blocking agent should be non-toxic, should remain at the surface of the skin or eye, and be non-absorbable. The blocking agent should cover the entire UV range of A, B and C radiation. Desirably, the blocking agent should reflect or at least diffract the infrared radiation known to potentiate the carcinogenic and inflammatory effect of the ultraviolet light. There is, therefore, substantial interest in developing sun blocking agents which approximate this ideal.

Relevant Literature

Dromgoole and Maibach, *J. Am. Academy of Dermatology*, Mosby Year Book, 1990, Chapter 8, describe contact sensitization and photocontact sensitization of sunscreening agents. Harber, et al., in *Photosensitivity Diseases, Principles of Diagnosis and Treatment*, B. Decker, Toronto, 1989, Chapter 10, page 141, describe intrinsic and extrinsic photoprotection against UV-B and UV-A radiation. Lowe, ibid., Chapter 11, page 161 describes the screening of various sun protection compositions.

In Japanese application No. 5-125118, filed Nov. 2, 1991, a para-amino benzoyl substituted polyacrylic acid as a sun blocking composition is reported, where a para-aminobenzoyl group is joined to the polyacrylic acid by a variety of linking groups. See also CA102:22131 1d which describes para-aminobenzoyl substituted acrylic polymers.

SUMMARY OF THE INVENTION

UV absorbing acrylic polymers are provided having a plurality of UV absorbing moieties which substantially cover the wave-length range of light (sunlight) which penetrates to the earth's surface. The polymers will normally include an additional monomer and may include a cross-linker. The polymers may be formulated in conventional ways. The formulations provide for long-term protection against erythema and other deleterious effects of UV radiation on the skin. The compositions may also find use in opthamalogical applications.

DESCRIPTION OF SPECIFIC EMBODIMENTS

Novel sun blocking polymeric compositions are provided comprising at least two different UV absorbing moieties and a hydrophilic moiety as substituents on the acrylic backbone. The compositions find use as sun blocking agents in a variety of contexts. The polymers may be prepared by combining the individual monomers under addition polymerizing conditions in appropriate amounts, taking into consideration the differential rates of incorporation of the different monomers, whereby a product is obtained having an effective proportion of monomers which absorb UV light in the wave length range to which skin is normally exposed on earth.

Normally, UV absorbers of at least UV-A and UV-B will be present, and desirably there will be an absorber for UV-C. In addition, there will be at least one other monomer which will have a hydrophilic substituent on the acryl group, particularly having one or more hydroxy groups. For the most part, the number ratio of total UV absorbers to other monomer(s) in the polymer will be in the range of about 0.1–10:1, usually 0.5–5:1, more usually 1–5:1. Of the UV absorbers present, there will generally be about 30–70 number of percent of the UV-B absorber, at least 20 number percent of the UV-A absorber, and the remainder being the UV-C absorber. Depending upon the individual monomers, the ratio of the UV absorbing monomers to the other monomers in the polymerization reaction mixture, the absence or presence of a cross-linking agent, and the like, the molecular weight may vary widely, where the composition of individual molecules may vary as the polymerization proceeds. To obtain high molecular weight polymer, it will be desirable to use small amounts of a cross-linking agent, generally from about 0.5–10 mole percent, more usually from about 1–3 mole percent of total monomer.

The polymeric composition will be insoluble in water, but desirably will swell in the aqueous formulation. Desirably, the polymer will swell in a polyethylene glycol (200–1000 mol. wt.)—water composition having from about 50–95 weight % polyethylene glycol. This can be readily achieved by appropriate ratios of the hydrophilic monomer to the UV absorbing monomers and the number of hydrophilic groups associated with the hydrophilic monomer. In addition, the UV monomers should have high extinction coefficients, at least about 20,000, preferably in excess of about 25,000.

The UV-A absorbers will, for the most part, be benzophenones or bis-benzoylmethane compounds, substituted with appropriate substituents for providing the desired light absorption characteristics, as well as for linking to the acryl group. For the most part, the UV-A absorbers of the subject composition will have the following formula:

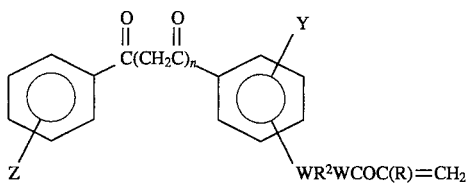

wherein:

n is 0–1;

R is H, alkyl of from 1 to 3, usually 1 to 2, carbon atoms, which may be substituted with a functional group having from 1 to 2 heteroatoms, which are N or O;

$R^2$ is a divalent hydrocarbylene group or substituted hydrocarbylene group, having up to 2, usually up to 1 substituent, where the substituent will be composed of oxygen, nitrogen, phosphorus, carbon and hydrogen, having from 1 to 3 heteroatoms, usually 1 to 2 heteroatoms, where the heteroatom may be in the chain, and from 0 to 6, usually 0 to 4 carbon atoms, which group may be aliphatic, alicyclic or aromatic, generally of from 2–8, more usually of from 2–6 carbon atoms, particularly phenylene or alkylene;

Z is oxy, particularly hydroxy or alkoxy of from 1–6, more usually 1–3 carbon atoms, or amino having from 0–2 alkyl substituents having a total of from about 1–12, more usually from about 1–6 carbon atoms, or hydrogen;

Z will preferably be at the para position to the carbonyl group;

Y is non-oxo carbonyl, which includes the carboxylic acid, carboxyl ester, where the ester will normally have an alkyl group of from 1–6, usually from 1–3 carbon atoms, or carboxamide, where the amino may be substituted or unsubstituted, where the substituted amino will have from 1–2 alkyl substituents with a total of from 1–12 carbon atoms, usually of from 1–6 carbon atoms;

Y is preferably at the ortho position in relation to the carbonyl;

W is oxy (—O—) or amino (—N($R^1$)), where $R^1$ is hydrogen or alkyl of from 1–6, usually 1–3 carbon atoms, where W is preferably oxy, when n is 1;

W is preferably substituted at the para position to the carbonyl;

there being from 0–2, usually 0–1 Y.

In addition, the rings may be substituted with from 0–3, usually 0–2 alkyl groups of from 1–6, more usually 1–3 carbon atoms, at available positions on the rings.

For the UV-B absorbers, the compounds for the most part will be benzoyloxy derivatives, particularly substituted benzoyloxy derivatives, more particularly para-amino substituted benzoyloxy derivatives. For the most part, these compounds will come within the following formula:

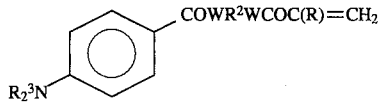

wherein:

$R^3$ is hydrogen or alkyl of from 1–6, usually 1–3 carbon atoms, preferably methyl; and W, R and $R^2$ are as defined previously.

The UV-C absorbing compound will be an oxybenzoyl derivative bonded to an acryl group through a divalent bridging moiety. For the most part, the UV-C absorbing group will have the following formula:

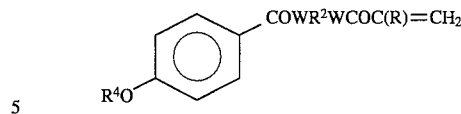

wherein:

$R^4$ is hydrogen or alkyl of from 1–6, usually 1–3 carbon atoms, preferably methyl, and the remaining symbols have been defined previously.

The remaining monomers will have at least one polar group, particularly an oxy group on a side chain. For the most part, these compounds will be relatively low molecular weight, generally being under about 400 Dal, more usually being under about 350 Dal. They will normally have at least 1 oxy group and may have up to 4 oxy groups, generally having from 1–3 oxy groups, more usually having from 1–3 hydroxy groups. For the most part, these compounds will have the following formula:

$$R^5WCOC(R)=CH_2$$

wherein:

$R^5$ is an aliphatic group of from 1–6, usually 1–4 carbon atoms having from 1–5, usually 1–3 oxy groups, more usually hydroxy groups;

the remaining symbols have been defined previously.

In the above formulas, the oxy or amino substituent may be substituted with a 2-nitrovinyl group to provide the desired radiation absorbing characteristics.

Compounds of interest include building blocks of p-aminobenzoic acid, p-methoxybenzoic acid, o-hydroxybenzoyl, p-dimethylaminobenzoic acid, p-aminobenzoyl, acetoxyhydroquinone, phenylenediamine, etc.

Compounds of interest include N,N-dialkylamino, N'-acryl or methacryl phenylenediamine, p-acryloxy or methacryloxybenzoate alkyl ester, N-alkyl m-acrylamido- or methacrylamidobenzoate alkyl ester, p-benzoyloxyacrylanilide or -methacrylanilide, p-acrylamido or -methacrylamidobenzoate methyl ester, o-acryloxy or -methacryloxydibenzoylmethane, p-acryloxy or -methacrylamidodibenzoylmethane, 4-acetoxy-1-acryloxy or -methacryloxybenzene, 2,4-dimethylamino-1-acryloxy or -methacryloxybenzene, N,N-bis-(3-acryloxy or -methacryloxyphenyl) methylamine, m-acryloxy or -methacryloxydibenzoylmethane, p,p'-diacryloxy or -methacryloxydibenzoylmethane, m,m'-diacryloxy or -methacryloxydibenzoylmethane, m,p'-diacryloxy or -methacryloxydibenzoylmethane, m- or p-acryloxy or -methacryloxy-2-nitrostyrene, 4-acryloxy or -methacryloxy-4'-(1"-(2"-nitrovinyl))dibenzoylmethane, and the like, where alkyl is 1–3, usually 1 carbon atom.

Any convenient cross-linking agent may be employed, which will usually be a bis-acryl or -methacryl, where the linking group may be any convenient group. Thus, the linking group may be methylene, amino, particularly substituted amino, 1,2-dioxyethylene, oxyamino, diaminoethylene, 1,4-dioxybutylene, dialkylenephosphate ester, α,α'-xylylenediamino, etc.

The subject monomers may be prepared from commercially available intermediates in accordance with known ways. A substantial number of starting monomers are provided in the accompanying working exemplification, which may serve as models for the production of a variety of monomers coming within the subject invention. In addition, the polymerization may be carried out in accordance with conventional ways, using free radical catalysts at relatively mild temperatures. Thus, peroxy compounds, azo compounds, ultraviolet light, or the like may be used as a source of polymerization initiation at temperatures in the range of about 10° to 70° C. for the polymerization. Usually, the polymerization will take place in the absence of oxygen, preferably under an inert atmosphere. The time for the polymerization will usually be at least an hour, usually at least 2 hours, and may extend to 24 hours or more, depending upon the conditions for the polymerization. A solvent may be used, e.g. an alkanol, particularly methanol, in which the various monomers are soluble. Generally, the solvent may be present in from about 0.2–10:1 weight ratio to the monomer charge. After completion of the polymerization, the polymer may be isolated in accordance with conventional ways, purified as appropriate, and then dried.

The subject polymers may be readily formulated with appropriate vehicles to provide the desired composition. The subject polymers may be formulated in creams, lotions, salves, and the like, to produce an adherent smooth invisible film and to partially diffract the UV and infrared radiation. A wide variety of emollients are taught in the literature and include polyethylene glycols, polypropylene glycols, and the like. Of particular interest is the use of other microparticles of other polymers, such as partially hydrolyzed polyacrylamides or ultrafine titanium or zinc oxides, although the latter do not absorb but only partially diffract or reflect UV light.

The polymers of the subject invention will be present in the formulation in at least about 5 weight percent and not more than about 70 weight percent, usually ranging from about 15–40 weight percent. The dermatological formulation may be coated, sprayed, spread or otherwise applied to the particular surface, e.g., skin, as required and will be retained at the surface for extended periods of time.

The following examples are offered by way of illustration and not by way of limitation.

EXPERIMENTAL

Example 1: Synthesis of an Acrylamide Derivative of an Carboxy-Substituted Benzophenone 40 g (210 mmol) of 2-aminobenzophenone-2'-carboxylic acid were placed in a L reaction flask followed by 500 ml of EtOH and 111 ml of 9.5N NaOH (1.05 moles). 100 ml of $H_2O$ were added to dissolve sodium salts. With stirring and cooling to 0°–5° C., 4.0 eq of acryloyl chloride were added over 10 minutes. The reaction was monitored by reverse phase HPLC. After completion, EtOH was removed by evaporation, and the reaction mixture acidified with HCl. A solid precipitated and was filtered. The yield of 2-acrylaminobenzophenone-2'-carboxylic acid was 53 g (86%).

Example 2: Acylation of 4-Amino Benzophenone with Acryloyl Chloride

4-Aminobenzophenone (10 g, 51 mmol, 1.00 eq) was dissolved in 40 ml of THF. After cooling to 5° C., acryloyl chloride (4.62 g, 51 mmol, 1.00 eq, in 10 ml THF) was added followed by triethylamine to scavenge the generated HCl.

THF was removed by rotary evaporation, the resulting oil was dissolved in 100 ml of ethyl acetate and the organic solution extracted with 3×50 ml of $H_2O$. Ethyl acetate was removed by rotary evaporation and the product was collected as a solid in a yield of 10.5 g (82%).

Example 3: N-acylation of p-hydroxyaniline with p-anisoyl chloride p-Hydroxy aniline (152.6 g, 1.398 moles) was dissolved in 1.9 L tetrahydrofuran and 113 ml (110.6 g, 1.398 moles) pyridine. p-Anisoyl chloride (238.5 g, 1.398 moles) was added dropwise at 20° C. over 2.5 hours. After stirring an additional 2 hours at 20° C., the solid was filtered and washed with tetrahydrofuran. The product, 466.5 g after drying, was refluxed in 3 L methanol for 1.5 hours, then cooled, filtered and washed with methanol. After vacuum drying, the solid weighed 262.8 g, yield 77%.

Example 4: Acylation of 4-methoxy-N-[1-(4-hydroxyphenyl)] benzamide with methacryloyl chloride 4-Methoxy-N-[1-(4-hydroxyphenyl)]benzamide (200 g, 0.8221 moles) was dissolved in 650 ml dimethylacetamide and triethylamine (91.52 g, 0.9043 moles) and then cooled to –15° C.. Methacryloyl chloride (94.53 g, 0.9043 moles) was added dropwise over an hour at –10° C. to produce a suspension. After warming to 20°–25° C., the suspension was diluted with 650 ml acetonitrile. The resulting solid was filtered, washed with acetonitrile and vacuum dried to 300 g and then refluxed in 1.5 L methanol for 1.5 hours. After cooling to 20°–25° C., the suspension was filtered, washed with methanol, and vacuum dried to 177 g of product, yield 69%.

Example 5: Acylation of 4-aminobenzoic acid with acryloyl chloride

4-Aminobenzoic acid (10.00 g, 0.073 moles) was dissolved in a mixture of water (20 ml), ethanol (50 ml) and 5N NaOH (37 ml). After cooling to 10° C., acryloyl chloride (8.58 g, 0.095 moles) was quickly added with stirring. Additional 1N NaOH (125 ml) and acryloyl chloride (8.58 g, 0.095 moles) were added to push the reaction to completion. The reaction was acidified to pH 1 with 6N HCl (25 ml) to produce a suspension that was filtered, washed with water and dried to a solid. Resuspension of the solid in acetonitrile (200 ml) at 60° C., followed by filtration, led to a solid product that weighed 10.1 g (Yield 72%) after vacuum drying.

Example 6: Amidation of 4-acrylamidobenzoic acid with aniline

4-Acrylamidobenzoic acid (1.91 2 g, 10 mmol) was dissolved in 10 ml chloroform and triethylamine (1.113 g, 11 mmol). After cooling to –25° C., chloroethylformate (1,193 g, 11 mmoles) in 3 ml chloroform was added dropwise with stirring. After 2 hours at –25 ° C., aniline (0.931 g, 10 mmoles) in 2 ml acetonitrile was added dropwise with stirring. The reaction was slowly warmed to 20° C., stirred for 16 hours, filtered, washed with chloroform, and dried to a mass of 1.46 g. This solid was dissolved in a mixture of ethyl acetate and isopentyl alcohol, and extracted twice with a bicarbonate solution. The organic layer was separated, dried over $MgSO_4$, filtered, and evaporated to dryness to give 1.30 g (50% yield).

Example 7: Amidation of 4-dimethylaminobenzoyl chloride with ethanolamine

4-Dimethylaminobenzoyl chloride(1.24 g, 6.75 mmoles) was dissolved in 15 ml tetrahydrofuran and then added dropwise to a stirred solution of ethanolamine (0.865 g, 14.17 mmoles) in 6 ml tetrahydrofuran held at –5 ° C.. After the 20 minute addition, the reaction was slowly warmed to 20°–25° C.. Tetrahydrofuran was removed in vacuo and the solids were stirred with 15 ml water for 25 minutes. The resulting product was filtered, washed with water and vacuum dried to 1.13 g. This solid was crystallized from N-propanol yielding 0.92 g (65%) of the desired product.

Example 8: Chlorination of 4-dimethylaminobenzoic acid

4-Dimethylaminobenzoic acid (250 g, 1.51 moles) was suspended in 2 L of ethyl acetate. Thionyl chloride (359.3 g, 3.02 moles) was added dropwise with stirring. After completion of the reaction, the solvent was removed by rotary evaporation affording a gray solid. The solid was crystallized from ethyl acetate to give 216 g of 4-dimethylaminobenzoyl chloride, yield 78%.

Example 9: Acylation of 2-hydroxyethyl methacrylate with 4-dimethylaminobenzoyl chloride 4-Dimethylaminobenzoyl chloride (21 6 g, 1.18 moles) was suspended 500 ml of ethyl acetate. 2-Hydroxyethyl methacrylate (169 g, 1.30 moles) was dissolved in 500 ml ethyl acetate and 165 ml triethylamine (119 g, 1.18 moles) and was added to the acid chloride with stirring. After completion of the reaction, the product was dissolved in ethyl acetate and extracted with dilute sodium bicarbonate. Ethyl acetate was removed by rotary evaporation and the crude product was crystallized from ethanol to give 188.9 g, yield 58%.

Example 10: Esterification of 4-hydroxydibenzoyl methane with methacryloyl chloride 4-Hydroxydibenzoyl methane (1.97 g, 8.2 mmol) was dissolved in 15 ml of ethyl acetate and 1.25 ml of triethylamine (0.91 g, 8.98 mmol). Methacryloyl chloride (0.98 g, 9.4 mmol) was dissolved in 5 ml of ethyl acetate and added dropwise with stirring. Triethylamine hydrochloride was removed by extraction and ethyl acetate was removed by rotary evaporation. Crystallization from ethanol yielded 1.65 g of product, yield 65%.

Example 11: 4-Tetrahydropyranyioxyacetophenone

4-Hydroxyacetophenone (75.00 g, 0.55 mol) was dissolved in ethyl acetate (300 ml) and a catalytic amount of methanesulfonic acid. The solution was cooled to 0°–4° C. Dihydropyran (204 ml, 2.20 moles, 4.0 eq) was slowly added. At the end of the addition, the ice-water bath was removed and the reaction was allowed to proceed at room temperature. A few minutes later a heavy white precipitate was formed and the slurry was transferred into a separatory funnel where it was washed with water. The organic layer was dried over anhydrous sodium sulfate. Removal of the solvent under reduced pressure afforded a white fluffy solid. The solid was recrystallized from hexane. The yield was quantitative.

Example 12: 4-Hydroxydibenzoyl methane

4-Tetrahydropyranloxyacetophenone (0.50 g, 2.11 mol) was dissolved in freshly distilled THF (6.0 ml). Sodium hydride (60% suspended in mineral oil, 170 mg, 4.23 mmol) was added. The mixture was stirred at room temperature and methyl benzoate (0.53 ml, 4.23 mmol) was added. The mixture was stirred at room temperature for an additional three hours. The reaction was quenched with the addition of methanol. After solvent removal, the crude oil was dissolved in methylene chloride and washed with a 0.02N aqueous solution of oxalic acid. The organic layer was then dried over anhydrous sodium sulfate. The crude product was dissolved in methanol (30 ml) and a 2N aqueous solution of oxalic acid (10 ml) was added. The solution was stirred for 2 hours at 42° C. The solvent was partially removed with the Rotavapor and a yellow solid was recovered upon filtration. The solid was dissolved in a minimum of hot ethanol and was precipitated by addition of hexane. A yellow solid (0.456 g, 1.90 mmol, 90%) was isolated.

Example 13: Acylation of 4-hydroxydibenzoylmethane with acryloyl chloride

4-Hydroxydibenzoyl methane (10.00 g, 41.62 mmol) was dissolved in freshly distilled THF (25.0 ml). The solution was cooled to 0° C. and diazobicycloundecene (DBU) (7.50 ml, 50.00 mmol) was slowly added at 0° C. Acryloyl chloride (5.92 ml, 72.84 mmol) was then added slowly at 0° C. After one hour stirring, the reaction was quenched by addition of methanol. Solvent removal afforded an oil. The crude oil was dissolved in a dichloromethane/hexane mixture. Purification was carried out by flash chromatography on silica gel utilizing hexane/dichloromethane as eluent. After pooling all relevant fractions and removing the solvent, a clear solid (5.60 g, 46%) was obtained.

Example 14: Acylation of p-hydroxymethacrylanilide with p-anisoyl chloride p-Hydroxymethacrylanilide (20.0 g, 113 mmol) was suspended in 250 ml ethyl acetate and 17.3 ml (12.6 g, 125 mmol) triethylamine. p-Anisoyl chloride (19.26 g, 113 mmol) was added dropwise at 25 ° C. over 15 minutes. The reaction was allowed to proceed for 24 hours with stirring at room temperature. The solid was filtered, washed with water (100 ml×3), and then washed with saturated bicarbonate solution (100 ml×3). The solid crystallized from methanol weighed 27.1 g, yield 77%.

Example 15: Acylation of 2-hydroxyethyl methacrylate with p-anisoyl chloride

2-Hydroxyethyl methacrylate (5.00 g, 38.5 mmol) was dissolved in 25.0 ml ethyl acetate and triethylamine (4.25 g, 42.0 mmol). p-Anisoyl chloride (6.48 g, 38,5 mmol) was added dropwise at 5 ° C. over ten minutes. After addition, the reaction was allowed to reach room temperature and stir for 24 hours. The triethylamine hydrochloride was filtered off and the filtrate washed with water (3×25.0 ml) and saturated bicarbonate solution (3×25.0 ml). The ethyl acetate layer was dried over $MgSO_4$, then stripped to a light yellow oil. The oil was distilled at 200° C. (0.1 mmHg) to yield the desired product.

Example 16: Acylation of N-2-hydroxyethyl acrylamide with p-anisoyl chloride

N-2-hydroxyethyl acrylamide (5.00 g, 43.4 mmol) was dissolved in 35.0 ml ethyl acetate and triethylamine (4.83 g, 47.7 mmol). p-Anisoyl chloride (7.40 g, 43.4 retool) was added dropwise at 5° C. over ten minutes. After addition, the reaction was stirred for 24 hours at room temperature. The solid was filtered and washed with water (3×25 ml), to remove triethylamine hydrochloride, followed by saturated bicarbonate solution (3×25 ml), and then dried (6.43 g). The initial ethyl acetate filtrate was washed with water (3×25 ml) and saturated bicarbonate solution (3×25 ml). Concentration of the ethyl acetate layer gave two further crops of crystals. Total yield of the three crops: 9.36 g, 93.6%.

Example 17: Acylation of N-[2-hydroxypropyl]methacrylamide with 4-dimethylaminobenzoyl chloride 4-Dimethylaminobenzoyl chloride (56.21 g, 0.306 mol) was combined with N-[2-hydroxypropyl]methacrylamide (42.96 g, 0.30 mol) and 250 ml acetonitrile. The mixture was stirred at room temperature and a solution was briefly obtained before the desired HCl salt of the product crystallized. After filtration, washing with cold acetonitrile and drying, 81.93 g (83.5 % yield) of product was obtained.

80.00 g (0.2447 mol) of the HCl salt was suspended in 400 ml dichloromethane while a solution of sodium bicarbonate (21.00 g, 0.25 mol) in 300 ml water was added dropwise. The two phases were filtered to remove turbidity and then separated. The $CH_2Cl_2$ layer was dried on $MgSO_4$, filtered, and evaporated to an oil that was crystallized from ethyl acetate to give 48 g of the free base of the product.

Example 18: Polymerization of a UV-A monomer, a UV-B monomer, and a UV-C monomer A 10 ml vial was charged with 4-methoxy-N-[1 -(4-methacryloxyphenyl)] benzamide (156 mg, 0.5 mmol); 4-(dimethylamino) benzoyloxyethyl methacrylate (138 mg, 0.5 mmol); 4-acryloxydibenzoyl methane (148 mg, 0.5 mmol); 2-hydroxyethyl methacrylate (98 mg, 0.75 mmol); N,N-methylene bis acrylamide (10 mg, 0.067 mmol); 2,2'-azobisbutyronitrile (3.7 mg, 0.022 mmol); and 3.5 ml methanol. The vial was flushed with argon, sealed and warmed to 60° C. for 20 hours with stirring. The resulting polymeric precipitate was filtered off, washed with methanol, dried to a mass of 0.50 g, and then ground to a fine light yellow powder.

Example 19: Polymerization of a UV-A monomer, a UV-B monomer, and a UV-C monomer A 1 liter flask was charged with 30.83 g (0.1 moles) UV-A monomer 4-methacryloxydibenzoyl methane, 29.04 g (0.1 moles) UV-B monomer N-[2-(4'-dimethylaminobenzoyl)oxy]propyl methacrylamide, 31.13 g (0.1 moles) UV-C monomer 4-methoxy-N-[1-(4-methacryloxyphenyl)] benzamide, 9.76 g (0.075 moles) 2-hydroxyethylmethacrylate, 1.73 g (0.01125 moles) N,N-methylene bisacrylamide, and 500 ml methanol. After flushing with argon, 0.951 g (0.00579 moles) of 2,'2-azobis butyronitrile was added along with 250 ml of MeOH. After stirring at 60° C. for 20 hours the sunscreen polymer was filtered, washed with methanol, and vacuum dried to a mass of 90,66 g.

Example 20: Formulation of a Polymeric Sunscreen 2.5 g of the polymeric sunscreen described in Example 19 was mixed with 6.0 ml of polyethylene glycol MW 400 and 0.3 ml $H_2O$ to produce a fine emulsion with the consistency of a spreadable paste. Upon skin application, the emulsion produced a well-adhering flexible and non-visible film.

In accordance with the invention, novel compositions are provided which give protection from erythema, carcinogenecity and other deleterious effects of ultraviolet radiation. The compositions have good retentive capability, provide a smooth coating on the skin, and do not unduly penetrate into the derreal layer, where the light absorbing moieties could have adverse effects. The compositions may be readily prepared from readily available compounds in accordance with conventional ways.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A polyacrylic acid based sunscreen composition having as its UV absorbing moieties:

for UV-A, a compound of the formula:

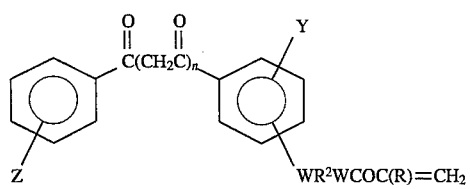

wherein:

n is 0 or 1;

Z is oxy or amino of not more than about than about 12 carbon atoms;

Y is non-oxo carbonyl of not more than about 12 carbon atoms; and

W is oxy or amino;

for UV-B, a compound of the formula:

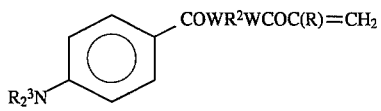

wherein:

$R^2$ is hydrogen or alkyl of up to 6 carbon atoms;

$R^3$ is a divalent hydrocarbylene group;

W and R are as defined above:

for UV-C, a compound of the formula:

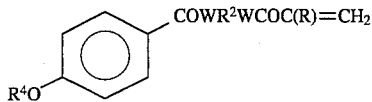

wherein:

$R^4$ is hydrogen or alkyl of from 1 to 6 carbon atoms; and the other symbols have been defined above; and an oxyaliphatic substituted acrylic acid of the formula:

wherein $R^5$ is an aliphatic group of from 1 to 4 carbon atoms having from 1 to 3 oxy groups, wherein the other symbols have been defined previously; and the polymer is insoluble in water and swellable in a polyethylene glycol-water composition comprising from about 50– 95% polyethylene glycol.

2. A polyacrylic acid according to claim 1, wherein the UV absorbers are from about 30–70 number % of UV-B, at least 20 number % UV-A, and the remainder UV-C and said polymer comprises from about 1 to 3 mole percent based on total monomer of a cross-linking acrylic monomer.

3. A sunscreen formulation comprising an effective amount for absorbing ultraviolet sunlight of a polyacrylic sunscreen having as its UV absorbing moieties;

for UV-A, a compound of the formula:

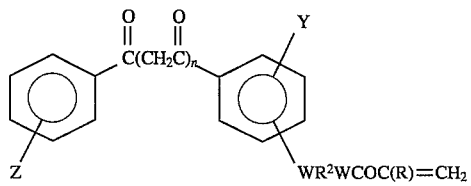

wherein:

n is 0 or 1;

R is H, alkyl of from 1 to 3 carbon atoms, which may be substituted with a functional group of from 0 to 3 carbon atoms having from 1 to 2N and O heteroatoms;

Z is oxy or amino of not more than about than about 12 carbon atoms;

Y is non-oxo carbonyl of not more than about 12 carbon atoms; and

W is oxy or amino;

for UV-B, a compound of the formula:

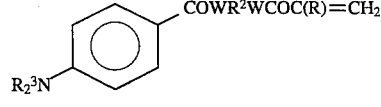

wherein:

$R^2$ is a divalent hydrocarbylene group or substituted derivative thereof;

$R^3$ is hydrogen or alkyl of up to 6 carbon atoms;

W and R are as defined above;

for UV-C, a compound of the formula:

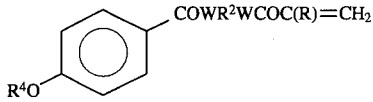

wherein:

$R^4$ is hydrogen or alkyl of from 1 to 6 carbon atoms; and the other symbols have been defined above; and an oxyaliphatic substituted acrylic acid of the formula:

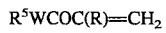

wherein $R^5$ is an aliphatic group of from 1 to 4 carbon atoms having from 1 to 3 oxy groups, wherein the other symbols have been defined previously; and the polymer is insoluble in water and swellable in a polyethylene glycol-water composition comprising from about 50–95% polyethylene glycol;

and a physiologically acceptable vehicle.

4. A sunscreen formulation according to claim 3, wherein said vehicle comprises a polypropylene glycol.

5. A sunscreen formulation according to claim 3, wherein said polyacrylic acid sunscreen is cross-linked with from about 1 to 3 percent of an acrylic cross-linking monomer and further comprises an hydroxyalkylacryl monomer.

* * * * *